(12) United States Patent
Rognes (10) Patent No.: US 7,917,302 B2
(45) Date of Patent: Mar. 29, 2011

(54) DETERMINATION OF OPTIMAL LOCAL SEQUENCE ALIGNMENT SIMILARITY SCORE

(75) Inventor: Torbjorn Rognes, Oslo (NO)

(73) Assignees: Torbjorn Rognes, Oslo (NO); Erling Christen Seeberg, Oslo (NO)

( * ) Notice: Subject to any disclaimer, the term of this patent is extended or adjusted under 35 U.S.C. 154(b) by 165 days.

(21) Appl. No.: 10/381,683

(22) PCT Filed: Sep. 27, 2001

(86) PCT No.: PCT/NO01/00394
§ 371 (c)(1),
(2), (4) Date: Mar. 27, 2003

(87) PCT Pub. No.: WO02/27638
PCT Pub. Date: Apr. 4, 2002

(65) Prior Publication Data
US 2004/0024536 A1    Feb. 5, 2004

(30) Foreign Application Priority Data
Sep. 28, 2000    (NO) .................................... 20004869

(51) Int. Cl.
*G01N 33/48*    (2006.01)
*G01N 31/00*    (2006.01)
*C12Q 1/68*    (2006.01)

(52) U.S. Cl. ................... 702/20; 702/22; 702/27; 435/6

(58) Field of Classification Search ........................ None
See application file for complete search history.

(56) References Cited

U.S. PATENT DOCUMENTS
5,485,627 A * 1/1996 Hillis ............................... 712/13
5,632,041 A    5/1997 Peterson et al.
6,044,419 A * 3/2000 Hayek et al. .................... 710/57

FOREIGN PATENT DOCUMENTS
EP        0 360 527    *   3/1990

OTHER PUBLICATIONS

Mount, David M. Bioinformatics: Sequence and Genome Analysis. Cold Spring Harbor Press, New York, 2000.*
Smith and Waterman. Journal of Molecular Biology. 1981 vol. 147, pp. 195-197.*
Rognes et al. Six-fold speed-up of Smith-Waterman sequence database searches using parallel processing on common microprocessors. Bioinformatics, vol. 18, 2000, pp. 699-706.*
Brutlag et al. BLAZE: An implementation of the Smith Waterman sequnce comparisom algorithm on a massively parallel computer. Computers & Chemistry, 1993, pp. 1-11 plus 6 graphics/captions pages.*
Nicholas et al. Strategies for searching sequence databases. BioTechniques, vol. 28, Jun. 2000, pp. 1174-1176, 1178, 1180, 1182, 1184-1186, 1188-1189, 1191.*
Hayes et al. Carbohydrate of the human plasminogen variants. The Journal of Biological Chemistry. vol. 254, 1979, pp. 8777-8780.*
Rognes, Torbjorn et al.: Six-fold speed up of Smith-Waterman sequence database searches using parallel processing on common microprocessors. In: Bioinformatics, vol. 16, No. 8, Aug. 2000, pp. 699-706. See whole document.
Martins, W. S. et al.: A multithreaded parallel implementation of a dynamic programming algoritym for sequence comparison. Pacific Symposium on Biocomputing 2001, Jan. 3-7, 2001. See the whole document.
Lavenier, Dominique: Dedicated hardware for biological sequence comparison. In: Journal of Universal Computer Science 2 (2) 1996. See p. 4 and figure 3.

* cited by examiner

*Primary Examiner* — Russell S Negin
(74) *Attorney, Agent, or Firm* — Harness, Dickey & Pierce, PLC (57) ABSTRACT

Sequence alignment and sequence database similarity searching are among the most important and challenging task in bio informatics, and are used for several purposes, including protein function prediction. An efficient parallelisation of the Smith-Waterman sequence alignment algorithm using parallel processing in the form of SIMD (Single-Instruction, Multiple-Data) technology is presented. The method has been implementation using the MMX (MultiMedia eXtensions) and SSE (Streaming SIMD Extensions) technology that is embedded in Intel's latest microprocessors, but the method can also be implemented using similar technology existing in other modern microprocessors. Near eight-fold speed-up relative to the fastest previously an optimised eight-way parallel processing approach achieved know non-parallel Smith-Waterman implementation on the same hardware. A speed of about 200 million cell updates per second has been obtained on a single Intel Pentium III 500 MHz microprocessor.

11 Claims, 5 Drawing Sheets

Fig. 3a query sequence / database sequence

Fig. 3b query sequence / database sequence

Fig.4a

| Pseudo-code | Comments |
|---|---|

```
FUNCTION PARALLELSW(S, DSEQ, q, r, m, n)
    BYTE S[x][m]
    BYTE DSEQ[n]
    INTEGER q,r,m,n

TYPEDEF BYTE VECTOR[8]

BYTE c
BYTE HH[m+1],EE[m]
INTEGER i,j,k
VECTOR H,E,F,LASTF,T1,T2,SCORE,ZERO,BASE,Q,R

ZERO  = [0, 0, 0, 0, 0, 0, 0, 0]
BASE  = [4, 4, 4, 4, 4, 4, 4, 4]
Q     = [q, q, q, q, q, q, q, q]
R     = [r, r, r, r, r, r, r, r]
SCORE = ZERO

FOR i = 0 TO m-1 DO
{
    HH[i] = 0
    EE[i] = 0
}

FOR j = 0 TO n-1 DO
{
    LASTF = ZERO
    c = DSEQ[j]
    H = HH[0 .. 7]

FOR i = 0 TO (m/8)-1 DO
    {
        H = H + S[c][8*i, ..., 8*i+7]
        H = H - BASE
        E = EE[8*i, ..., 8*i+7]
        H = MAX(H , E)

T1 = MAX(LASTF, H) - Q - R
        IF (any element of T1 > 0) THEN
        {
            F = (H SHIFT +1) OR LASTF
            F = F - Q - R
            T2 = F FOR k = 1 TO 7 DO
            {
                T2 = (T2 - R) SHIFT +1
                F = MAX(F , T2)
            }

H = MAX(H , F)
            E = MAX(E , H - Q) - R
            SCORE = MAX(SCORE, H)
            LASTF = MAX(H , F + Q)
            LASTF = LASTF SHIFT -7
        }
        ELSE
        {
            E = E - R
            LASTF = H SHIFT -7
        }

EE[8*i, ..., 8*i+7] = E

TEMP = HH[8*i+8 .. 8*i+15]
        HH[8*i+1, ..., 8*i+8] = H
        H = TEMP
    }
}

RETURN max(SCORE[0], SCORE[1], ..., SCORE[7])
```

Comments:

S is a query-specific score matrix (x is alphabet size)
DSEQ is the database sequence
q and r are gap open and extension penalties
m and n are query and database sequence lengths Single database sequence symbol (c)
Arrays (HH,EE)
Loop indices (i,j,k)
Vectors (H,E,F,LASTF,T1,T2,SCORE,ZERO,BASE,Q,R)

Zero vector (constant)
Score base vector (constant)
Gap open penalty vector (constant)
Gap extension penalty vector (constant)
Initialise score vector to zero Initialise HH-array with zero
Initialise EE-array with zero For each symbol in the database sequence...

Initialize LASTF-vector for first round
Get one database symbol
Load H-vector from HH-array For each vector of 8 matrix cells along query sequence:

Add query score profile vector to H vector
Subtract base vector
Load E-vector from EE-array
Replace H by largest elements from H and E Check if any element of H or LASTF is above q+r
If so, compute correct H and F vectors:

Compute initial F-vector by combining LASTF with H0-6
Subtract gap penalty of single symbol gap (q+r)
Copy F into temporary Repeat for all remaining vector elements:

Subtract gap extension penalty (r) from temporary vector and shift
Replace F by largest elements from F and temporary Replace H by largest elements from H and F
Update E-vector
Update SCORE-vector
Replace LASTF by largest elements from H and F+Q
Shift LASTF for use in next round If no values above q+r, just do the following:

Update E-vector by subtracting gap extension penalty
Shift H for use as in next round and save in LASTF Save E-vector in EE-array Load vector from HH-array into temporary to prevent overwrite
Save H-vector in HH-array
Move temporary vector into H-vector Return largest element of the score vector

Fig. 4b

DETERMINATION OF OPTIMAL LOCAL SEQUENCE ALIGNMENT SIMILARITY SCORE

FIELD OF INVENTION

The present invention relates to the comparison of biological sequences and, more specifically, the invention relates to a method, a computer readable device and an electronic device for determination of optimal local sequence similarity score in accordance with the claims.

BACKGROUND OF INVENTION

The rapidly increasing amounts of genetic sequence information available represent a as constant challenge to developers of hardware and software database searching and handling. The size of the GenBank/EMBL/DDBJ nucleotide database is now doubling at least every 15 months (Benson et al. 2000). The rapid expansion of the genetic sequence information is probably exceeding the growth in computing power available at a constant cost, in spite of the fact that computing resources also have been increasing exponentially for many years. If this trend continues, increasingly longer time or increasingly more expensive computers will be needed to search the entire database.

Searching databases for sequences similar to a given sequence is one of the most fundamental and important tools for predicting structural and functional properties of uncharacterised proteins. The availability of good tools for performing these searches is hence important. When looking for sequences in a database similar to a given query sequence, the search programs compute an alignment score for every sequence in the database. This score represents the degree of similarity between the query and database sequence. The score is calculated from the alignment of the two sequences, and is based on a substitution score matrix and a gap penalty function. A dynamic programming algorithm for computing the optimal local alignment score was first described by Smith and Waterman (1981), improved by Gotoh (1982) for linear gap penalty functions, and optimised by Green (1993).

Database searches using the optimal algorithm are unfortunately quite slow on ordinary computers, so many heuristic alternatives have been developed, such as FASTA (Pearson and Lipman, 1988) and BLAST (Altschul et al., 1990; Altschul et al., 1997). These methods have reduced the running time by a factor of up to 40 compared to the best-known Smith-Waterman implementation on non-parallel general-purpose computers, however, at the expense of sensitivity. Because of the loss of sensitivity, some distantly related sequences might not be detected in a search using the heuristic algorithms.

Due to the demand for both fast and sensitive searches, much effort has been made to produce fast implementations of the Smith-Waterman method. Several special-purpose hardware solutions have been developed with parallel processing capabilities (Hughey, 1996), such as Paracel's Gene Matcher, Compugen's Bioccelerator and TimeLogic's DeCypher. These machines are able to process more than 2 000 million matrix cells per second, and can be expanded to reach much higher speeds. However, such machines are very expensive and cannot readily be exploited by ordinary users. Some hardware implementations of the Smith-Waterman algorithm are described in patent publications, for instance U.S. Pat. Nos. 5,553,272, 5,632,041, 5,706,498, 5,964,860 and 6,112,288.

A more general form of parallel processing capability is available using Single-Instruction Multiple-Data (SIMD) technology. A SIMD computer is able to perform the same operation (logical, arithmetic or other) on several independent data sources in parallel. It is possible to exploit this by dividing wide registers into smaller units in the form of micro parallelism (also known as SIMD within a register—SWAR). However, modern microprocessors have added special registers and instructions to make the SIMD technology easier to use. With the introduction of the Pentium MMX (MultiMedia eXtensions) microprocessor in 1997, Intel made computing with SIMD technology available in a general-purpose microprocessor in the most widely used computer architecture—the industry standard PC. The technology is also available in the Pentium II and has been extended in the Pentium III under the name of SSE (Streaming SIMD Extensions) (Intel, 1999). Further extension of this technology has been announced for the Pentium 4 processor (also known as Willamette) under the name SSE2 (Streaming SIMD extensions 2) (Intel 2000). The MMX/SSE/SSE2 instruction sets include arithmetic (add, subtract, multiply, min, max, average, compare), logical (and, or, xor, not) and other instructions (shift, pack, unpack) that may operate on integer or floating-point numbers. This technology is primarily designed for speeding up digital signal processing applications like sound, images and video, but seems suitable also for genetic sequence comparisons. Several other microprocessors with SIMD technology are or will be made available in the near future, as shown in table 1 (Dubey, 1998).

TABLE 1

Examples of microprocessors with SIMD technology

| Manufacturer | Microprocessor | Name of technology |
|---|---|---|
| AMD | K6/K6-2/K6-III | MMX/3DNow! |
|  | Athlon/Duron | Extended MMX/3DNow! |
| Compaq (Digital) | Alpha | MVI (Motion Video Instruction) |
| Hewlett Packard (HP) | PA-RISC | MAX(-2) (Multimedia Acceleration eXtensions) |
| HP/Intel | Itanium (Merced) | SSE (Streaming SIMD Extensions)? |
| Intel | Pentium MMX/II | MMX (MultiMedia eXtensions) |
|  | Pentium III | SSE (Streaming SIMD Extensions) |
|  | Pentium 4 | SSE2 (Streaming SIMD Extensions 2) |
| Motorola | PowerPC G4 | Velocity Engine (AltiVec) |
| SGI | MIPS | MDMX (MIPS Digital Media eXtensions) |
| Sun | SPARC | VIS (Visual Instruction Set) |

Several investigators have used SIMD technology to speed up the Smith-Waterman algorithm, but the increase in speed relative to the best non-parallel implementations have been limited.

The general dynamic programming algorithm for optimal local alignment score computation was initially described by Smith and Waterman (1981).

Gotoh (1982) described an implementation of this algorithm with affined gap penalties, where the gap penalty for a gap of size k is equal to q+rk, where q is the gap open penalty and r is the gap extension penalty. Under these restrictions the running time of the algorithm was reduced to be proportional to the product of the lengths of the two sequences.

Green (1993) wrote the SWAT program and applied some optimisations to the algorithm of Gotoh to achieve a speed-up of a factor of about two relative to a straightforward implementation. The SWAT-optimisations have also been incorporated into the SSEARCH program of Pearson (1991).

The Smith-Waterman algorithm has been implemented for several different SIMD computers. Sturrock and Collins (1993) implemented the Smith-Waterman algorithm for the MasPar family of parallel computers, in a program called MPsrch. This solution achieved a speed of up to 130 million matrix cells per second on a MasPar MP-1 computer with 4096 CPUs and up to 1 500 million matrix cells per second on a MasPar MP-2 with 16384 CPUs. Brutlag et al. (1993) also implemented the Smith-Waterman algorithm on the MasPar computers in a program called BLAZE.

Alpern et al. (1995) presented several ways to speed up the Smith-Waterman algorithm including a parallel implementation utilising micro parallelism by dividing the 64-bit wide Z-buffer registers of the Intel Paragon i860 processors into 4 parts. With this approach they could compare the query sequence with four different database sequences simultaneously. They achieved more than a fivefold speedup over a conventional implementation.

Wozniak (1997) presented a way to implement the Smith-Waterman algorithm using the VIS (Visual Instruction Set) technology of Sun UltraSPARC microprocessors. This implementation reached a speed of over 18 million matrix cells per second on a 167 MHz UltraSPARC microprocessor. According to Wozniak (1997), this represents a speedup of a factor of about 2 relative to the same algorithm implemented with integer instructions on the same machine.

Taylor (1998 and 1999) applied the MMX technology to the Smith-Waterman algorithm and achieved a speed of 6.6 million cell updates per second on an Intel Pentium III 500 MHz microprocessor.

Sturrock and Collins (2000) have implemented the Smith-Waterman algorithm using SIMD on Alpha microprocessors. However no details of their method has been published. They have achieved a speed of about 53 million cell updates per second using affine gap penalties. It is unknown exactly what computer this system is running on.

Recently, Barton et al. (2000) employed MMX technology to speed up their SCANPS implementation of the Smith-Waterman algorithm. They claim a speed of 71 million cell updates per second on a Intel Pentium III 650 MHz microprocessor. Only a poster abstract without any details of their implementation is currently available.

DISCLOSURE OF THE INVENTION

It is described an efficient parallelisation related to a method for computing the optimal local sequence alignment score of two sequences. Increased speed of the overall computation is achieved by performing several operations in parallel.

The invention enables Smith-Waterman based searches to be performed at a much higher speed than previously possible on general-purpose computers.

Using the MMX and SSE technology in an Intel Pentium III 500 MHz microprocessor, a speed of about 200 million cell updates per second was achieved when comparing a protein with the sequences in a protein database. As far as known, this is so far the fastest implementation of the Smith-Waterman algorithm on a single-microprocessor general-purpose computer. Relative to the commonly used SSEARCH program, which is consider as a reference implementation, it represents a speedup of about eight. It is believed that an implementation of the present invention on the forthcoming Intel Pentium 4 processor running at 1.4 GHz will obtain a speed of more than 1000 million cell updates per second.

These speeds approach or equal the speed of expensive dedicated hardware solutions for performing essentially the same calculations.

Using the present invention, high speed is achieved on commonly available and inexpensive hardware, thus significantly reducing the cost and/or computation time of performing sequence alignment and database searching using an optimal local alignment dynamic programming approach.

Figure 2A:
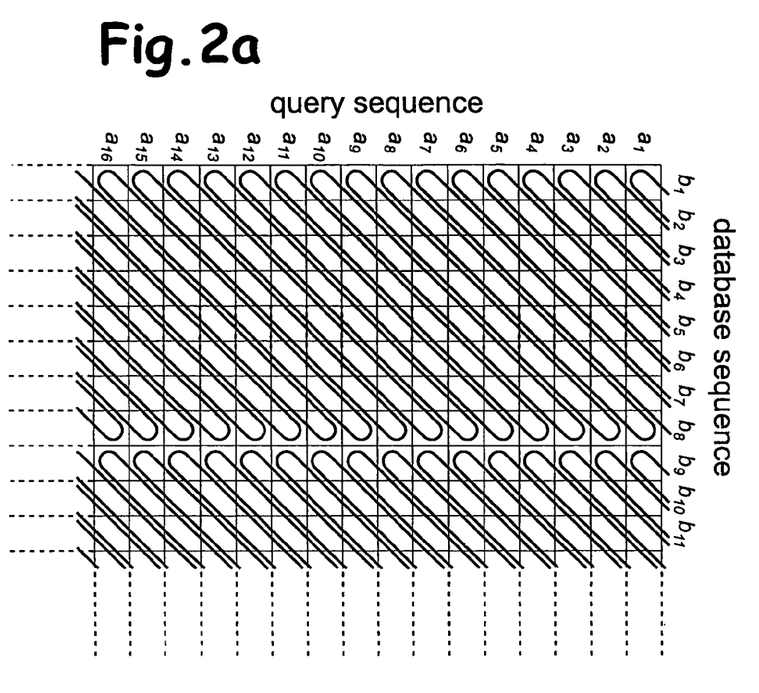
FIG. 2 illustrates vector arrangements in SIMD implementations of the Smith-Waterman algorithm, each column represent one symbol of the database sequence, and each row represents on symbol of the query sequence, where
 a) represent traditional approach with vectors parallel to the minor diagonal in the matrix, and
 b) represents the novel approach with vectors parallel to the query sequence.
Figure 2B:
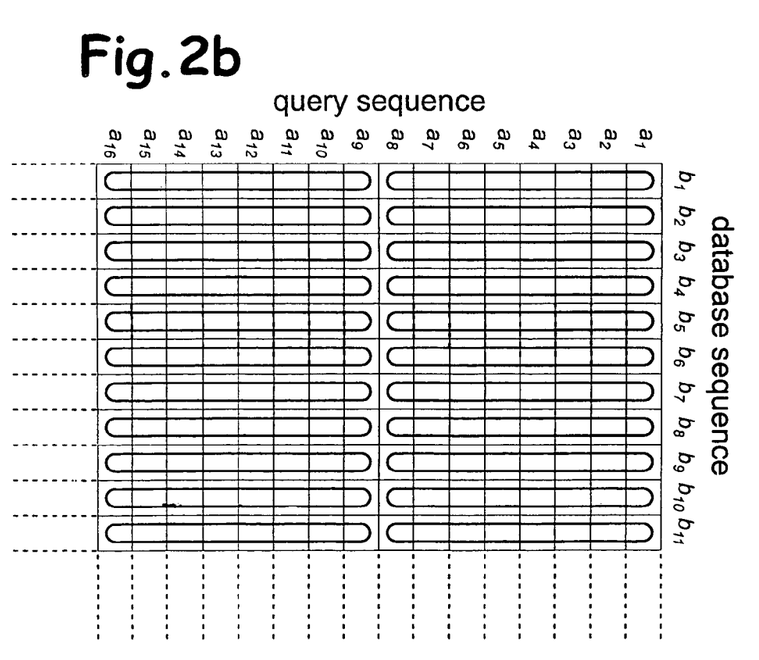

The present invention is based on the principle that all calculations are performed using vectors that are parallel to the query sequence ("query-based vectors") (see FIG. 2b). This is in contrast to the traditional approach in which the calculations are performed using vectors that are parallel to the minor diagonal in the matrix ("diagonal vectors") (see FIG. 2a). In both cases, the vectors contain two or more elements that represent different cells in the alignment matrix. The values in the elements of the vectors represent score values, e.g. the h-, e- or f-variables in the recurrence relations described later.

Figure 3A:
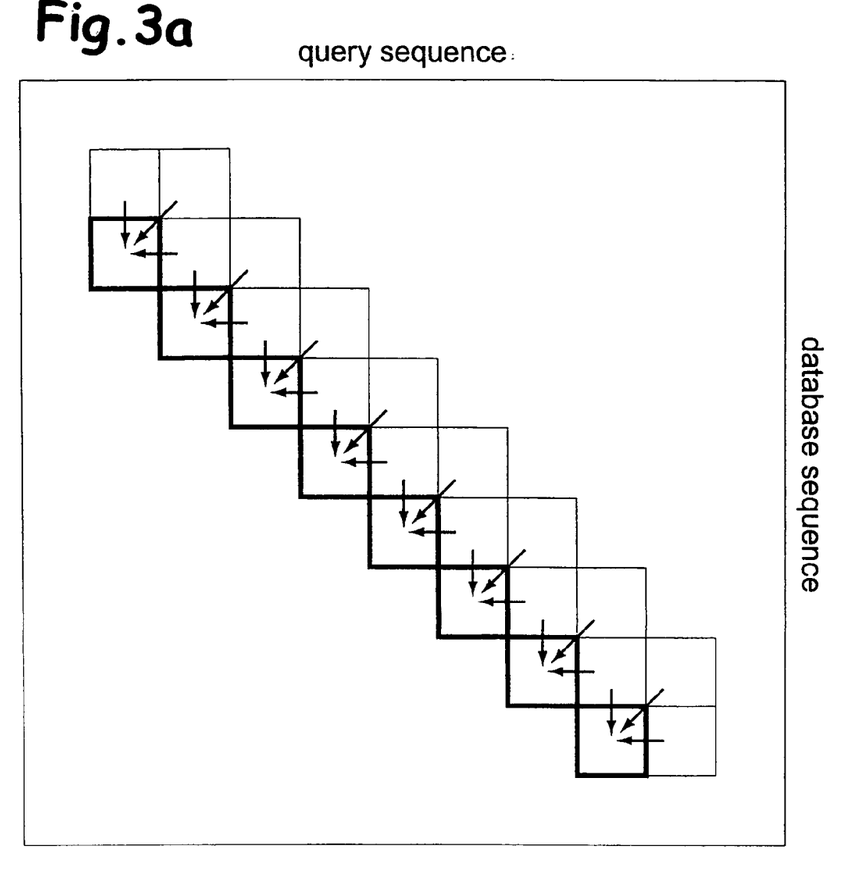
FIG. 3 illustrates vector calculation dependencies, the arrows indicates dependencies between matrix cells that are involved in the computations of the h-, e- and f-values in the elements of the vector using (a) the traditional and (b) the novel approach.

The advantage of the traditional approach is that the calculations of the individual elements of the vectors are completely independent (see FIG. 3a). Hence the use of this approach may seem obvious. The traditional approach is described in detail by Hughey (1996), Wozniak (1997) and Taylor (1998, 1999), and seems to be almost universal to all parallel implementations of the Smith-Waterman alignment procedure that are known in detail. However, there are several disadvantages with this approach, most notably the complexity of forming the vector of substitution score values. This problem is especially noticeable at high degrees of parallelism. The query-based vector approach has not been described earlier, in spite of numerous attempts to parallelise the Smith-Waterman algorithm. It is believed that the present invention is sufficiently novel and different from the current "state of the art".

Figure 3B:
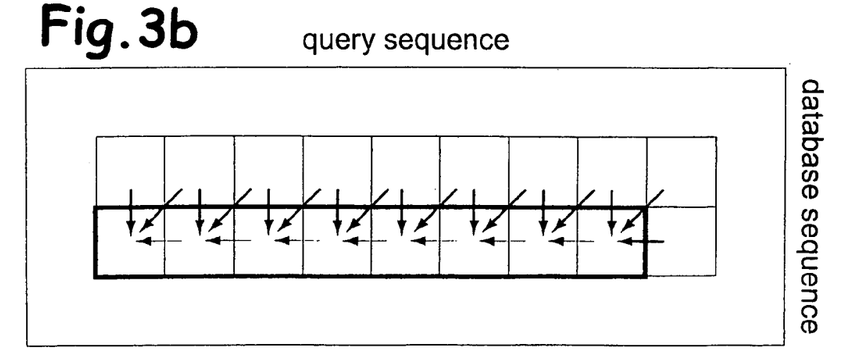

The disadvantage of the query-based vector approach is the dependence between the individual vector elements in some of the calculations (see FIG. 3b). However, by exploiting a vector generalisation of the principles used in the SWAT-optimisations, these dependencies will only affect a small fraction of the calculations, and hence not have a major impact on the performance. The advantage of the query-based approach is the greatly simplified loading of the vector of substitution score values from memory when using a query sequence profile (also known as a query-specific score matrix).

The present invention method uses a query profile, which is a matrix of scores for all combination of query positions and possible sequence symbols. The scores are arranged in memory in such a manner that a vector representing the scores for matching a single database sequence symbol with a consecutive range of query sequence symbols can easily be loaded from memory into the microprocessor using a single instruction. This is achieved by first storing the scores for matching the first possible database sequence symbol with each of the symbols of the query sequence, followed by the scores for matching the second possible database sequence symbol with each query position, and so on.

The scores in the query profile are all biased by a fixed amount (e.g. 4, in case of the BLOSUM62 matrix) so that all values become non-negative, and stored as an unsigned integer. This allows subsequent calculations to be performed using unsigned arithmetic. The constant bias is later subtracted using an unsigned integer subtraction operation.

Vector elements are represented by few bits (e.g. 8), and may thus represent only a narrow range of scores. When the total vector size is limited to a specific number of bits (e.g.

64), narrow vector elements allows the vector to be divided into more elements (e.g. 8) than if wider elements were used. This allows more concurrent calculations to take place, further increasing speed.

In order to make the narrow score range useful even in cases where the scores are larger than what can be represented by a vector element, we employ saturated arithmetic to detect overflow in the score calculations. If overflow is detected, the entire alignment score is subsequently recomputed using an implementation with a wider score range, e.g. 16 bits. Because such high scores are relatively rare, the performance impact is small.

Score computations are performed using unsigned values. Unsigned score values allows the widest possible score range. This reduces the number of recomputations necessary as described above.

The computations are performed using saturated unsigned arithmetic. This allows easy clipping of negative results of subtractions at zero, an operation that is frequently performed in the calculations.

The method, the computer readable device and the electronic device have their respective characteristic features as stated in the claims.

BRIEF DESCRIPTIONS OF DRAWINGS

FIG. 4a illustrates pseudo-code for the new approach, the pseudo-code being just a detailed example showing how our method may be implemented in a computer program.

FIG. 4b illustrates a flow diagram of the pseudo-code in FIG. 4a

TABLE 2

The symbols and phrases used in the pseudo-code.

| Phrase/statement/symbol | Description |
| --- | --- |
| BYTE a | Indicates that the variable a is represented by a byte (8 bits) value |
| INTEGER a | Indicates that the variable a is a variable able to represent integer values |
| BYTE A[m] | Indicates that A is an array of m elements, where each element is represented by a byte value |
| BYTE A[m][n] | Indicates that A is a two-dimensional array (matrix), where each element is represented by a byte value |
| VECTOR A | Indicates that A is a vector of containing eight elements, each represented by a byte value |
| a = b | The variable a is assigned the value of expression b |
| A = B | The vector variable A is assigned the value of expression B. Can be implemented using the MOVQ (move quadword) instruction on processors supporting MMX technology. |
| (A + B) − C | Parenthesises indicated expressions that take precedence in the order of computation. |
| FUNCTION a(b, c) ... RETURN c | The FUNCTION and RETURN statements indicate the beginning and ending of a function a taking b and c as parameters and returning the resulting value c. |
| FOR i = a TO b DO {     statements } | This FOR-statement indicates that the statements enclosed by the brackets should be repeated (b−a+1) times, with a loop index variable i, taking consecutive integer values a., a+1, a+2, ..., b−1, b. |
| IF expression THEN {     if-statements } ELSE {     else-statements } | This IF-statement indicates that the if-statements shall be executed if the expression is true, and that the else-statements shall be executed if the expression is false. |
| { ... } | Brackets enclosing the statements of a for-loop, if-statements and else-statements |
| a + b | An expression representing the sum of the values of a and b |
| a − b | An expression representing the value of b subtracted from the value of a |
| a * b | Indicates scalar integer multiplication |
| a/b | Indicates scalar integer division |
| max (a, b, c, ...) | A scalar expression representing the largest of its arguments |

TABLE 2-continued

The symbols and phrases used in the pseudo-code.

| Phrase/statement/symbol | Description |
| --- | --- |
| A + B | A vector operation taking A and B as arguments and representing a new vector where each element is equal to the pair wise sum of the corresponding elements of vector A and B. The computations are performed using unsigned saturated arithmetic, meaning that if any resulting element is larger than the highest representative number, that element is replaced by the largest representative integer.<br>$c_i = \min(a_i + b_i, 255)$<br>Can be implemented using the PADDUSB (packed addition of unsigned saturated bytes) instruction on processors supporting MMX technology. |
| A − B | A vector operation taking A and B as arguments and resulting in a new vector where each element is equal to the pair wise difference between the corresponding elements of vector A and B, when subtracting each value of B from the value of A. The computations are performed using unsigned saturated arithmetic, meaning that if the difference is negative, zero replaces the result.<br>$c_i = \max(a_i - b_i, 0)$<br>Can be implemented using the PSUBUSB (packed subtract of unsigned saturated bytes) instruction on processors supporting MMX technology. |
| MAX (A , B) | A vector operation taking A and B as arguments and representing a new vector where each element is equal to the larger of two corresponding elements of A and B.<br>$c_i = \max(a_i, b_i)$<br>Can be implemented using the PMAXUB (packed maximum unsigned byte) instruction processors supporting SSE technology, or using the PSUBUSB instruction followed by the PADDUSB (packed subtract/add unsigned saturated bytes) instruction on processors supporting only MMX technology. |
| A SHIFT b | SHIFT is a vector operation taking the vector A and the scalar b as arguments and resulting in a new vector where the elements of vector A is shifted a number of positions. Element i of vector A is placed at position i+b in the new vector. The remaining elements of the resulting vector are assigned a value of zero. Thus:<br>IF ( (i>=b) AND (i<b+x))<br>    { $c_i = a_{i-b}$ }<br>ELSE<br>    { $c_i = 0$ }<br>The sign of b hence indicates the direction of the shift, while the magnitude of b indicates the number of positions the elements shall be shifted.<br>On Intel Pentium processors and other little-endian microprocessors, a positive b value corresponds to a left shift, while a negative b-value corresponds to a right shift. On big-endian microprocessors the shift direction is reversed.<br>Can be implemented using the PSLLQ and PSRLQ (packed shift left/right logical quadword) instructions on processors supporting MMX technology. |
| A OR B | Bit wise OR of all bits in vector A and B.<br>Used in combination with the SHIFT-operation to combine elements from two vectors into a new vector. |
| A[i] | An expression representing element number i of vector or array A |
| A[b .. c] | An expression representing a vector containing elements at position b to c of the array A. |
| [a, b, c, d, e, f, g, h] | An expression representing a vector consisting of elements with values a, b, c, d, e, f, g, and h. |

PREFERRED EMBODIMENT OF THE INVENTION

The preferred embodiment will be described with reference to the drawings. For each sequence in the database, a sequence similarity-searching program computes an alignment score that represent the degree of similarity between the query sequence and the database sequence. By also taking the length and composition of the query and database sequences into account, a statistical parameter can be computed and used to rank the database sequences in order of similarity to the query sequence. The raw alignment score is based on a substitution score matrix, (e.g. BLOSUM62), representing the similarity between two symbols, and an affined gap penalty function based on a gap open and a gap extension penalty.

In the following description vectors of 8 elements are used with 8 bits each, totalling 64 bits. However, this is only for the ease of description. Many other combinations of vector and element sizes are possible and can easily be generalised from the description below. Any number of vector elements larger than one, and any number of bits for each element is possible. However, an element size of 8 bits, and a vector size of 8, 16 or 32 elements are probably the most useful.

In the following description the method is illustrated with a possible implementation using Intel's microprocessors and their MMX and SSE technology. However, this is just for the ease of description. An implementation using other microprocessors and other SIMD technology is also possible.

The Smith-Waterman Algorithm

To compute the optimal local alignment score, the dynamic programming algorithm by Smith and Waterman (1981), as enhanced by Gotoh (1982), is used. Given a query sequence A of length m, a database sequence B of length n, a substitution score matrix Z, a gap open penalty q and a gap extension penalty r, the optimal local alignment score t can be computed by the following recursion relations:

$$e_{i,j} = \max\{e_{i,j-1}, h_{i,j-1} - q\} - r$$

$$f_{i,j} = \max\{f_{i-1,j}, h_{i-1,j} - q\} - r$$

$$h_{i,j} = \max\{h_{i-1,j-1} + Z[A[i], B[j]], e_{i,j}, f_{i,j}, 0\}$$

$$t = \max\{h_{i,j}\}$$

Here, $e_{i,j}$ and $f_{i,j}$ represent the maximum local alignment score involving the first i symbols of A and the first j symbols of B, and ending with a gap in sequence B or A, respectively. The overall maximum local alignment score involving the first i symbols of A and the first j symbols of B, is represented by $h_{i,j}$. The recursions should be calculated with i going from 1 to m and j from 1 to n, starting with $e_{i,j} = f_{i,j} = h_{i,j} = 0$ for all i=0 or j=0. The order of computation of the values in the alignment matrix is strict because the value of any cell cannot be computed before the value of all cells to the left and above it has been computed, as shown by the data interdependence graph in FIG. 1. An implementation of the algorithm as described by Gotoh (1982) has a running time proportional to mn.

Parallelisation

Figure 1:
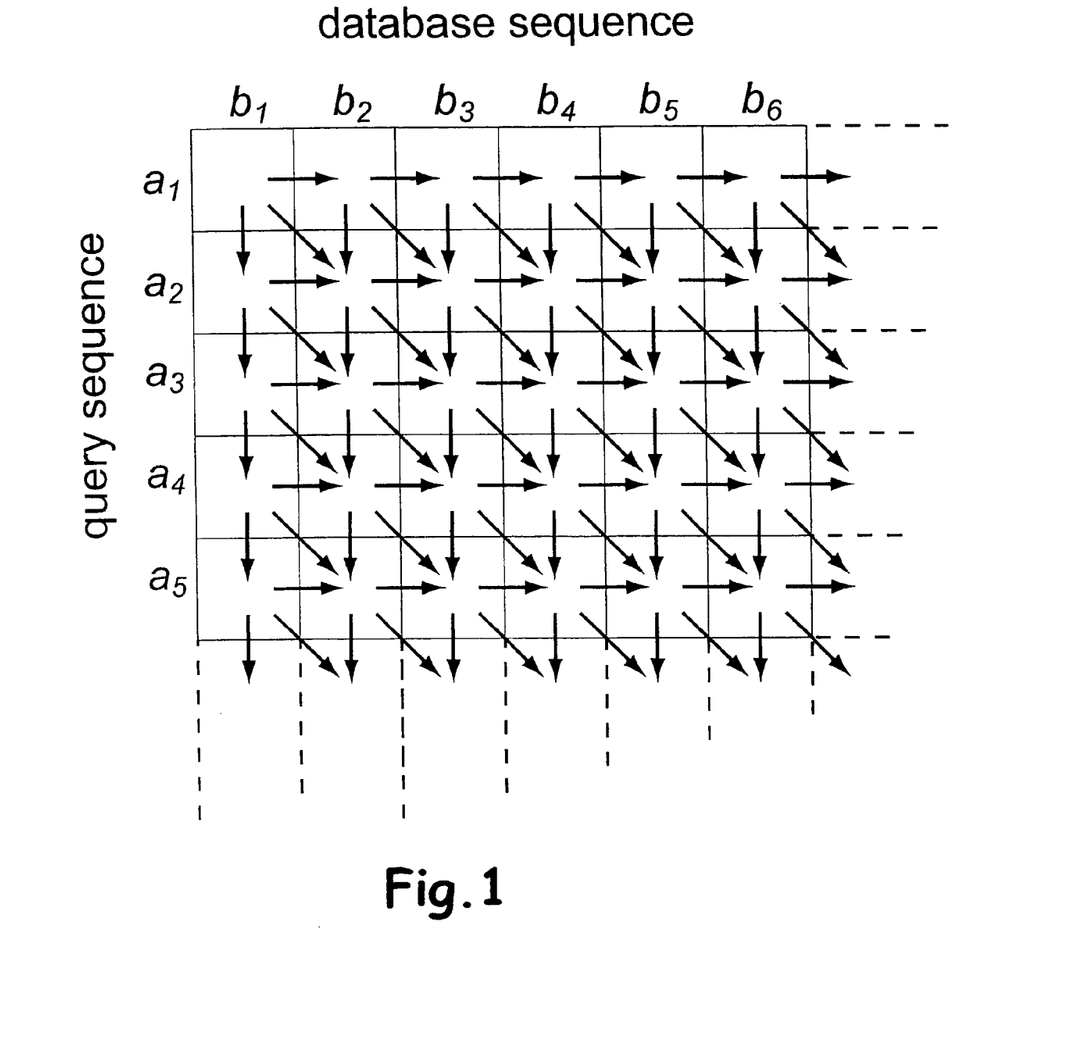
FIG. 1 illustrates computational dependencies in the Smith-Waterman alignment matrix, the arrows indicate dependencies between matrix cells that are involved in the computations of the h-, e- and f-values in each cell of the alignment matrix.

The Smith-Waterman algorithm can be made parallel on two scales. It is fairly easy to distribute the processing of each of the database sequences on a number of independent processors in a symmetric multiprocessing (SMP) machine. On a lower scale, however, distributing the work involved within a single database sequence is a bit more complicated. FIG. 1 shows the data interdependence in the alignment matrix. The final value, h, of any cell in the matrix cannot be computed before the value of all cells to the left and above it has been computed. But the calculations of the values of diagonally arranged cells parallel to the minor diagonal (see FIGS. 2a and 3a) are independent and can be done simultaneously in a parallel implementation. This fact has been utilised in earlier SIMD implementations (Hughey, 1996; Wozniak, 1997).

The Inventive Approach

The main features of the implementation according to the invention, are:

Vectors parallel to the query sequence
Vector generalisation of the SWAT-optimisations
8-way parallel processing with 8-bit values
Query sequence profiles
Unsigned arithmetics
Saturated arithmetics
General code optimisations These concepts are described in detail below. In order to illustrate and exemplify the description, pseudo-code for the present method is shown in FIG. 4.

Figure 4B:
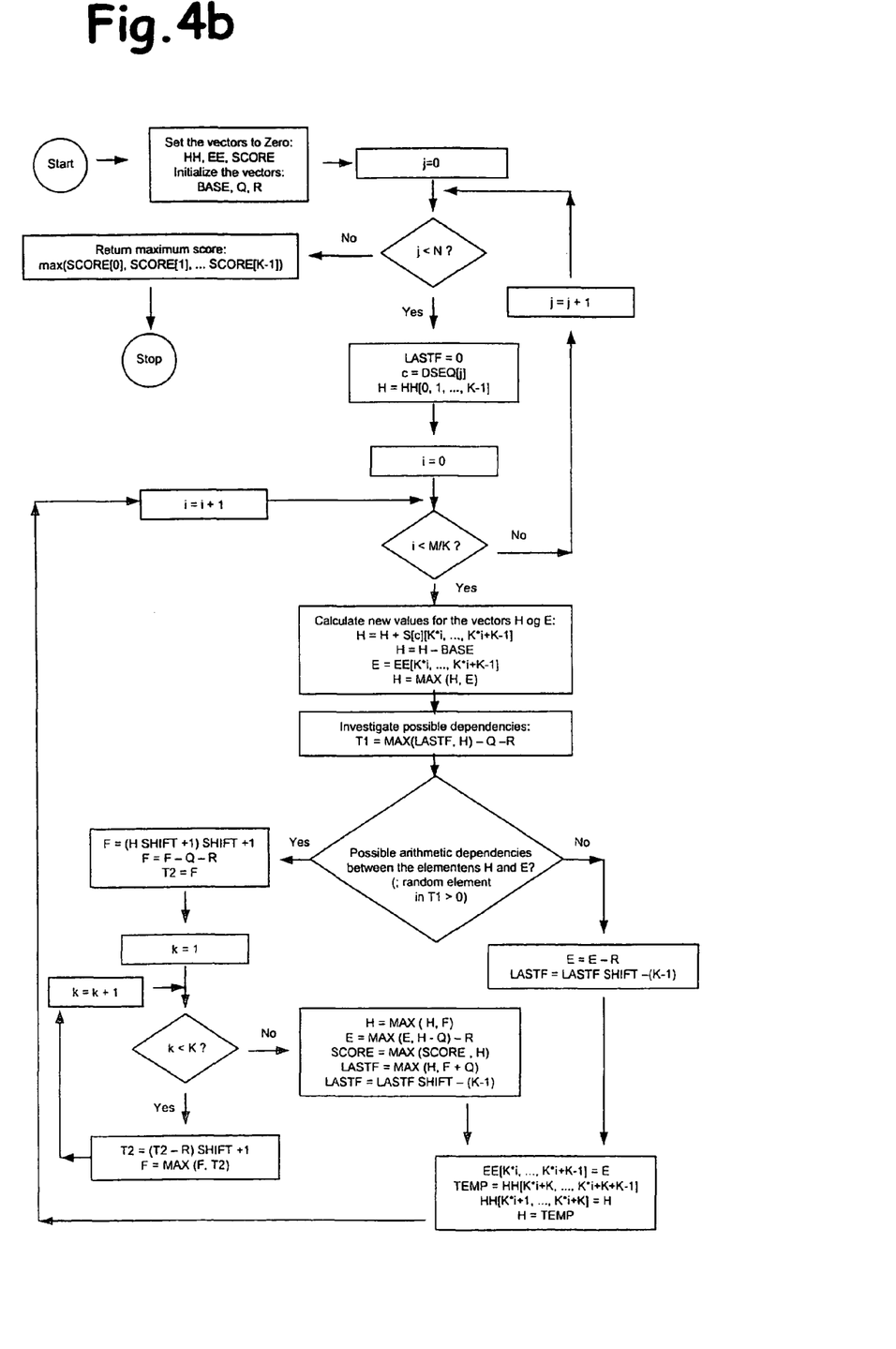

In the pseudo-code, the method according to the invention through FIGS. 4a and 4b, is illustrated using vectors of 8 elements, however the present invented method is general and can be implemented with vectors of any number of elements.

The pseudo-code assumes that the query sequence length (m) is a multiple of the vector size, 8. This can be achieved by padding the query sequence and query score profile.

All vector indices start at zero as is usual in programming languages (not one, as is usual in ordinary mathematics notation).

Upper case letters are generally used to represent vector or array variables or operations, while lower case letters are generally used to represent scalar variables or operations.

The S-matrix is an x times n query-specific score matrix representing the score for substituting any of the x different possible database sequence symbols with the query symbol at any of the n query positions. In general, x just represents the size of the alphabet from which the sequence symbols belong to. For amino acid sequences, x is typically 20 (representing the 20 natural amino acids) or slightly larger (to include also ambiguous and other symbols). For nucleotide sequences, x is typically 4 (representing the 4 nucleotides adenine, cytosine, guanine and thymine/uracil), or larger (to include also ambiguous and other symbols). The S-matrix is usually precomputed from a query sequence and a substitution score matrix, but may also represent a general query profile, which may be based on scores calculated from a multiple alignment of a protein sequence family.

The H-vectors holds the h-values, representing the optimal local alignment score for a given matrix cell. The H-vectors represent a part of the HH-array. The E-vector holds the e-values, representing scores from alignments involving a database sequence gap. The E-vectors represent a part of the EE-array. The F-vector holds the f-values, and temporary f-values, representing scores from alignments involving a query sequence gap.

In the LASTF vector, only a single element (at index 0) is used. It represents the potential score from previous rounds involving a gap in the query sequence. The actual value used has the gap opening penalty added, in order to simplify later calculations.

Vectors Parallel to the Query Sequence

Despite the loss of independence between the computations of each of the vector elements, it was decided to use vectors of cells parallel to the query sequence (as shown in FIGS. 2b and 3b), instead of vectors of cells parallel to the minor diagonal in the matrix (as shown in FIGS. 2a and 3a). The advantage of this approach is the much-simplified and faster loading of the vector of substitution scores from memory. The disadvantage is that data dependencies within the vector related to the f-value computations (see FIG. 3b) must be handled. Eight cells are processed simultaneously along each column as indicated in FIG. 2b. Vectors are used to represent the h-, e- and f-values in the recurrence relations in groups of eight consecutive cells parallel to the query sequence. Vectors are also used to represent zero, q, r, q+r and other constants. Using vector processing, the value of eight h-, e- or f-values may be computed in parallel (the h, e and f as described in the equations on page 11).

Vector Generalisation of the SWAT-Optimisations

As already indicated, we have to take into account that each element in the vector is dependent on the element above it, as shown in FIG. 3b, because of the possible introduction of gaps in the query sequence. We employ a vector generalisation of the SWAT-optimisations and other optimisations to make the principle of query-parallel vectors efficient. The concept is illustrated in the pseudo-code in FIG. 4.

The f-values represent the score of an alignment ending at a cell with a gap in the query sequence. The f-values are dependent on the h- and f-values in the cells above it. Hence, the F-vector is dependent on the H- and F-vectors, and in addition, on the h- and f-value in the cell immediately above the vector. These dependencies make the calculations complex and hard to do in parallel in the general case.

However, because the h-value of a cell may only influence other cells if the h-value is larger than a threshold equal to the gap penalty of a single symbol gap (q+r), the calculations may be simplified in most cases. In practice, relatively few of the cells have h-values that are above the threshold, implying that simplified calculations can be used in most cases. These principles can be generalised in the vector case.

It is possible to quickly check if there is a possible dependency problem or not for the entire vector. If the check is negative (possible dependency), we have to do the complex calculations to find the correct h-, e- and f-values. If the check is positive (no dependency), most of the calculations can be skipped.

To check whether there is a possible dependency, it is first computed an initial H-vector without taking the f-values into account. By examining the initial H-vector and the h- and f-value from the cell immediately above the vector, it can be decided if there will be any dependence between the cells. If the value of any element in the H-vector is greater than the q+r threshold, there is a possible dependency. There is also a possible dependency if the h-value in the cell above the vector is greater than the q+r threshold, or if the f-value in the cell above the vector is greater than the gap extension penalty, r.

Actually, the bottom element of the initial H-vector cannot cause any intra-vector dependency, but we include it in the check, because it affects the E-vector and the vector containing the overall highest scores.

If the check is positive, the initial H-vector is also the final H-vector. In this case, the E-vector is also not dependent on the H-vector and can be computed simply by deducting the gap extension penalty from each element of the E-vector. If the check is positive, we can also skip updating the vector containing the overall highest scores (unless we are interested in final scores below q+r).

If the check is negative, the correct F-vector has to be computed based on the initial H-vector, and the h- and f-values from the cell above. This computation is performed by a lengthy series of subtraction-, shift-, and maximum-operations as described by the pseudo-code in FIG. 4. When the correct F-values have been computed, the correct H- and E-vectors must be updated. In addition the vector containing the overall highest scores must also be updated.

8-Way Parallel Processing with 8-Bit Values

The microprocessors provide for the SIMD instructions a set of registers (usually 64-bit wide) that can be divided into smaller units. The Pentium family of microprocessors contains several 64-bit registers that can be treated either as a single 64-bit (quad word) unit, or as two 32-bit (double word), four 16-bit (word), or eight 8-bit (byte) units. Operations on these units are independent. Hence, the microprocessor is able to perform up to eight independent additions or other operations simultaneously.

In order to optimise the speed of the calculations, the MMX-registers of the microprocessor could be divided into as many units as possible, i.e. eight 8-bit units. This allows eight concurrent operations to take place. Dividing the MMX-registers into eight 8-bit registers increases the number of parallel operations but limits the precision of the calculations to the range 0-255. Unless the sequences are long and very similar, this poses no problems. In the few cases where this score limit is surpassed, the use of saturation arithmetic (see below) will ensure that the overall highest score will stay at 255. For all sequences that reach a score of 255, the correct score may subsequently be recomputed by a different implementation with a larger score range (e.g. using a non-SIMD implementation).

Query Sequence Profiles

Initially we compute a query profile (also known as a query-specific score matrix) called S, which is an m times x matrix, with the following values:

$$S[k, i] = Z[k, A[i]]$$

Here k is any of the possible symbols occurring in sequence B, and i is the query position. This profile is computed only once for the entire search. The score for matching e.g. symbol A (for alanine) in the database sequence B with each of the symbols in the query sequence is stored sequentially in the first matrix row, followed by the scores for matching symbol B (ambiguous) in the next row, and so on. This query sequence profile is used extensively in the inner loop of the algorithm and is usually small enough to be kept in the microprocessor's first level cache.

Unsigned Arithmetic

In most microprocessors, additions and subtractions can be performed in either unsigned or signed mode. In the inner loop of the algorithm, the query profile scores are added to the unsigned h-values. Using a signed addition, the h-values would have been restricted to the range of 0-127. Instead, all the values in the query sequence score profile were biased by a fixed amount (e.g., 4) so that no values were negative. One signed operation was then replaced by an unsigned addition followed by an unsigned subtraction of the bias. The useful data range was hence expanded to nearly 8 bits (e.g., 0-251).

Saturated Arithmetic

Unsigned arithmetic using SIMD technology can be performed in either a modular (also known as wrap-around) or in a saturated mode. When using 8-bit wide registers, subtracting 25 from 10 will give the result 241 (because 10-25=241-256) in modular mode and 0 in saturated mode. This is very useful in the inner loop calculations of the Smith-Waterman algorithm because zero in some of the calculations should replace negative results. Also, because of the limited precision of a single byte value, saturated arithmetics are useful to detect potential overflow in the calculations with very high scores.

The core of the Smith-Waterman algorithm repeatedly computes the maximum of two numbers. It is therefore important to make this computation fast. The SSE instruction set includes a special instruction (pmaxub) that computes the largest of two unsigned bytes. This instruction was not included in the original MMX instruction set, but can be replaced by an unsigned saturated subtraction (psubusb) followed by an unsigned saturated addition (paddusb).

General Code Optimisations

In order to get complete control over code optimisation and because of limited support for the SIMD instructions in high-level languages, the core of the algorithm should be written in assembly language.

The use of conditional jumps should be avoided when it is difficult for the microprocessor to predict whether to jump or not, because mispredictions require additional time. In addition, conditional jumps based on the results of MMX/SSE operations are not straightforward on the Intel architecture because the status flags are not set by these instructions.

In order to achieve the highest speed, the memory used repeatedly in the calculations should preferably be contained in the first level caches of the microprocessor. In addition to the query sequence score profile, the vectors storing the h and e values from the last column should also fit in the cache, but these are usually only about 400 bytes each for an average sequence.

The 64-bit memory accesses used with MMX registers should preferably be placed on 8 byte boundaries, in order to be as fast as possible. We have taken this into account when aligning the data structures. Code alignment also had substantial effects on the speed.

When the computer is equipped with enough internal memory to hold the entire database, the use of memory-mapped files is an effective way to read the database. The entire sequence file can then be mapped to particular address range in memory. Operating systems are usually optimised for reading sequential files in this way.

Application Areas and Industrial Utilisation

The present method can in general be used in any form of comparison of two linear sequences of symbols, representing one-dimensional signals, i.e. genetic or biological molecules, sound signals (e.g. speech, voice, music), text in any language (human, computer), or other phenomenon. However, comparison of nucleotide or amino acid sequences is the most obvious application. It can be used both for direct pair wise sequence comparison (alignment) and for database similarity searching. The method quantifies the amount of similarity between two sequences, and can be used to find which sequences in a database that is the most similar to a given sequence. The most similar sequences are often related or homologous to the query sequence.

The following types of comparisons and database searches are possible:

- Comparison/alignment of amino acid sequences (proteins, enzymes).
- Comparison/alignment of nucleotide sequences (DNA, RNA, mRNA, cDNA, etc.).
- Database searching, in which a nucleotide query sequence is compared to all nucleotide sequences in a database, a score is computed for each database sequence, and the database sequences with scores of interest are reported.
- Database searching, in which an amino acid query sequence is compared to all amino acid sequences in a database.
- Comparison of a protein query sequence with nucleotide sequences in a database, after translating the database sequences into all six frames, also taking possible frame shifts into account.
- Comparison of a nucleotide query sequence with amino acid sequences in a database, after translating the query sequence into all six frames, also taking possible frame shifts into account.
- Comparison of a nucleotide query sequence with nucleotide sequences in a database, after translating both the query sequence and the database sequences into all six frames, also taking possible frame shifts into account.

Other variants of the present invented method are also possible:

- Sequence alignment or database searching where the query sequence is replaced by a query profile, e.g. a matrix of scores for every combination of query position and possible database sequence symbol
- Sequence alignment where our method is applied to a band or otherwise restricted area in the alignment matrix
- Sequence database similarity searching where our method is applied to a subset of the database after a pre-filtering procedure is applied to all database sequences
- Sequence database similarity searching where our method is applied to a query sequence that has been filtered or masked to remove regions of repetitive sequences, biased composition or other low-complexity regions
- An implementation of the inventive method where the resulting scores for each database sequence is the basis for the calculation of a statistical parameter indicating the significance of each match, by also taking into account the length and/or composition of the query and database sequences, in addition to the scoring scheme (choice of substitution matrix and gap penalty function)
- An implementation of the inventive method on a symmetric multiprocessing (SMP) computer
- An implementation of the inventive method on a cluster of networked computers
- An implementation of the inventive method on a microprocessor with missing or limited explicit instructions for SIMD operations, by using SIMD within a register (SWAR) or other forms of microparallelism
- As a part of an iterative database homology search application, similar to e.g. PSIBLAST (Altschul et al 1997), in which the sequence information from a family of sequences is used to detect distantly related sequences The present method can be used as a part of the following applications within bio informatics:

- Protein function prediction
- Protein structure prediction
- RNA function prediction
- RNA structure prediction
- Multiple sequence alignment
- Sequence clustering
- Protein family grouping/clustering
- DNA sequence contig assembly
- Detection of coding sequence regions in nucleotide sequences
- Phylogenetic tree construction
- Any other applications which involves computation of an accurate sequence alignment score The present method can also be used in the following product:

- a general-purpose computer system containing software that implements the described algorithm.

Equivalents to the above product are:

- other computer systems using a digital signal processing device implementing the described method
- dedicated hardware solutions in the form of electronic circuits that incorporates the described method, e.g. an application specific integrated circuit (ASIC), field-programmable gated arrays (FPGA), or custom very large scale integration (VLSI) chips. Using VHDL hardware description language of the method outlined in this disclosure of the invention, any form of electronic device implementation of the method can be achieved as long as the VHDL synthesize tool support the chosen technology as is well known to a person skilled in the art.

REFERENCES

Alpern, B., Carter, L. and Gatlin, K. S.(1995) Microparallelism and High Performance Protein Matching. In *Proceedings of the 1995 ACM/IEEE Supercomputing Conference*: San Diego, Calif., Dec. 3-8, 1995.

Altschul, S. F., Gish, W., Miller, W., Myers, E. W. and Lipman, D. J. (1990) Basic local alignment search tool. *J. Mol. Biol.*, 215, 403-410.

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. *Nucleic. Acids. Res.*, 25, 3389-3402.

Bairoch, A. and Apweiler, R. (2000) The SWISS-PROT protein sequence database and its supplement TrEMBL in 2000. *Nucleic. Acids. Res.*, 28, 45-48.

Barton G., Webber C., Searle, S. M. J. (2000) New Developments to SCANPS: High Performance Parallel Iterated Protein Sequence Searching with Full Dynamic Programming and on-the-fly Statistics. Intelligent Systems for Molecular Biology (ISMB) 2000. (poster) (unpublished)

Benson D. A., Karsch-Mizrachi I., Lipman D. J., Ostell J., Rapp B. A., and Wheeler D. L. 2000) GenBank. *Nucleic. Acids. Res.* 28, 15-18.

Brutlag, D. L., Dautricourt, J. P., Diaz, R., Fier, J., Moxon, B. and Stamm, R. (1993) BLAZE: An implementation of the Smith-Waterman Sequence Comparison Algorithm on a Massively Parallel Computer. Computers & Chemistry, 17, 203-207.

Dubey, P. K. (1998) Architectural and design implications of mediaprocessing,

Gish, W. (1996) WU-BLAST.

Gotoh, O. (1982) An improved algorithm for matching biological sequences. *J. Mol. Biol.*, 162, 705-708.

Green, P. (1993) SWAT.

Henikoff, S. and Henikoff, J. G. (1992) Amino acid substitution matrices from protein blocks. *Proc. Natl. Acad. Sci U.S.A.*, 89, 10915-10919.

Hughey, R. (1996) Parallel hardware for sequence comparison and alignment. *Comput. Applic. Biosci.*, 12, 473-479.

Intel (1999) Intel Architecture Software Developer's manual; Volume 2: Instruction Set Reference.

Intel (2000) IA-32 Intel Architecture Software Developer's Manual With Preliminary Willamette Architecture Information; Volume 2: Instruction Set Reference.

Karlin, S. and Altschul, S. F. (1990) Methods for assessing the statistical significance of molecular sequence features by using general scoring schemes. *Proc. Natl. Acad. Sci. USA*, 87, 2264-2268.

Motorola (1998) AltiVec Technology Programming Environments Manual. http://www.mot.com/SPS/PowerPC/teksupport/teklibrary/manuals/altivec_pem.pdf Pearson, W. R. (1991) Searching protein sequence libraries: comparison of the sensitivity and selectivity of the Smith-Waterman and FASTA algorithms. *Genomics*, 11, 635-650.

Pearson, W. R. and Lipman, D. J. (1988) Improved tools for biological sequence comparison. *Proc. Natl. Acad. Sci U.S.A.*, 85, 2444-2448.

Rognes, T. and Seeberg E. (2000) Six-fold speed-up of Smith-Waterman sequence database searches using parallel processing on common microprocessors. *Bioinformatics*. In press.

Smith, T. F. and Waterman, M. S. (1981) Identification of common molecular subsequences. *J. Mol. Biol.*, 147, 195-197.

Sturrock S. S. and Collins J. F. (1993) MPsrch V1.3 User Guide. Biocomputing Research Unit, University of Edinburgh, UK.

Sturrock S. S. and Collins J. F. (2000) MPsrch V4.0. Biocomputing Research Unit, University of Edinburgh, UK. Unpublished.

Taylor S. (1998) Architecture and Implementation for Optimization of the Smith-Waterman Algorithm using Single-Instruction, Multiple-Data (SIMD) instructions.

Taylor S. (1999) Applying MMX Technology to the Smith-Waterman Algorithm.

Wootton, J. C. and Federhen, S. (1993) Statistics of local complexity in amino-acid sequences and sequence databases. Computers & Chemistry, 17, 149-163.

Wozniak, A. (1997) Using video-oriented instructions to speed up sequence comparison. *Comput. Appl. Biosci.*, 13, 145-150.

The invention claimed is:

1. A computer-implemented method for measuring similarity between two polynucleotide sequences or two amino acid sequences, the two sequences represented as sequence A of M elements and sequence B of N elements to be used in a Smith-Waterman local alignment similarity score calculations, comprising calculating a score S based on an alignment matrix H of M times N elements by using a substitution score value matrix Z, an open penalty gap q and a gap extension penalty r, where the calculation of the alignment matrix H comprises the steps of a) using K elements located sequentially on the same row or column in the alignment matrix H, and
   b) providing vectors V with the K elements where the vectors V are represented as registers or processing elements in a microprocessor, thereby enabling parallel processing of K elements, and
   c) determining if the calculation of the value of any one of the said K elements in one of said vectors is dependent on the value of any of the different K−1 elements in said one vector or on a value in an element from a different vector, the determination comprising the steps of:
      (i) calculating initial score values for the K elements of the said vector by ignoring any effect that could have resulted from potential gaps in the sequence in the direction of the said vector; and
      (ii) determining if dependency is possible by checking whether the last element of the previous vector or any but the last of said initial values exceed a limit formed as the sum of the gap open penalty and gap extension penalty parameters, and
   d) computing the vector element values without taking potential gaps in the direction of the vector into account if no dependency is detected, or
   e) recursively computing the optimized values by taking potential gaps in the direction of the vector into account if dependency is detected, and
   f) using a maximum range of values in the storage element representing one of said K elements, comprising applying only non-negative values in the processing of said K elements by adding a bias if the starting value is negative, applying only unsigned arithmetic in the processing of said K elements, and subtracting the same bias later on, said bias being equal to the absolute value of the largest representation of negative value in the element storing said one of said K elements, and
   g) outputting the score S to a user, a display, a memory, or a computer in a network, and wherein every method step is performed by a suitably programmed computer.

2. The computer implemented method according to claim 1 further comprising the step of:

handling overflow in one storage element including said one K element by employing saturated arithmetic to detect overflow in score calculations, and, if overflow is detected, the entire alignment score is subsequently recomputed using a score range in the storage element including the said one K element that is wider than the score range used in the storage element including the said one K element when overflow is detected.

3. The computer implemented method according to claim 2 further comprising the step of:

detecting overflow in said arithmetic operations by applying saturated arithmetic and adjusting the value to the maximum representation of value in the storage element representing said one K element when overflow of the data type of the storage element occurs, thereby detecting overflow by recognizing this maximum representation of value in said one storage element.

4. A computer memory containing computer instructions executable by a suitably programmable computer to perform a method for measuring similarity between two polynucleotide sequences or two amino acid sequences, the two sequences represented as a-sequence A of M elements and a sequence B of N elements to be used in a Smith-Waterman optimal local alignment similarity score implemented algorithm among the computer instructions comprising calculating a score S based on an alignment matrix H of M times N elements by using a substitution score value matrix Z and an open penalty gap q and a gap extension penalty r, wherein the computer memory for the calculation of the alignment matrix H comprises computer instructions that:
  a) allocate K elements located sequentially on the same row or column in the alignment matrix H, and
  b) create vectors V with the K elements where the vectors V are represented as registers or processing elements in a microprocessor, that can execute the computer instructions, and
  c) provide parallel processing of the K elements, and
  d) determine if the calculation of the value of any one of the said K elements in one of said vectors is dependent on the value of any of the different K−1 elements in said one vector or on a value in an element from a different vector, the determination comprising the steps of:
    (i) calculating initial score values for the K elements of the said vector by ignoring any effect that could have resulted from potential gaps in the sequence in the direction of the said vector; and
    (ii) determining if dependency is possible by checking whether the last element of the previous vector or any but the last of said initial values exceed a limit formed as the sum of the gap open penalty and gap extension penalty parameters, and
  e) compute the vector element values without taking potential gaps in the direction of the vector into account if no dependency is detected, or
  f) recursively compute the optimized values with taking potential gaps in the direction of the vector into account if dependency is detected, and
  g) use a maximum range of values in the storage element representing one of said K element, comprising applying only non-negative values in the processing of said K elements by adding a bias if the starting value is negative, applying only unsigned arithmetic in the processing of said K elements, and subtracting the same bias later on, said bias being equal to the absolute value of the largest representation of negative value in the element storing said one of said K elements, and
  h) output at least score S to a user by said computer readable memory.

5. The computer memory according to claim 4, said computer memory further comprising the computer instructions of:
  dividing the registers in a microprocessor in said K elements where these elements are operated on simultaneously by using one or more instructions with the same arithmetic or logic operation on all the said K elements such that the said operation on one of the said K elements does not influence the result of the same simultaneous said operation on another of the said K elements.

6. The computer memory according to any one of claims 4 and 5, said computer memory further including the instructions of:
  handling overflow in one storage element including said one K element employing saturated arithmetic to detect overflow in score calculations, and, if overflow is detected the entire alignment score is subsequently recomputed using a score range in the storage element including the said one K element that is wider than the score range used in the storage element including the said one K element when overflow is detected.

7. The computer memory according to claim 6, said computer memory further including the instructions of:
  detecting overflow in said arithmetic operations by applying saturated arithmetic and adjusting the value to the maximum representation of value in the storage element representing said one K element when overflow of the data type of the storage element occur thereby detecting overflow by recognizing this said maximum representation of value in said storage element.

8. The computer memory according to any one of claims 4 to 5, said computer memory further comprises instructions operable to
  optimize selected ones of said computer instructions with SIMD (Single Instruction Multiple Data) program code.

9. An electronic device of type ASIC (Application Specific Integrated Circuitry) providing measuring of similarity between two polynucleotide sequences or two amino acid sequences, the two sequences represented as a sequence A of M elements and a sequence B of N elements wherein means in the ASIC provide a Smith-Waterman optimal local alignment similarity score implemented algorithm calculating a S score based on alignment of a matrix H of M times N elements by using a substitution score value matrix Z, and an open penalty gap q and a gap extension penalty r, wherein means in the ASIC for the calculation of alignment matrix H comprises means that:
  a) allocate the K elements located sequentially on the same row or column in the alignment matrix H, and
  b) create vectors V with the K elements where the vectors V are represented as registers or processing elements in a microprocessor, that can execute the computer instructions, and
  c) include means for parallel processing of the K elements, and
  d) report at least score S; and
  e) the electronic device further comprises circuitry for determining if the calculation of the value of any one of the said K elements in one of said vectors is dependent on the value of any of the different K−1 elements in said one vector or on a value in an element from a different vector, including circuitry for:
    (i) calculating initial score values for the K elements of the said vector by ignoring any effect that could have resulted from potential gaps in the sequence in the direction of the said vector; and
    (ii) determining if dependency is possible by checking whether the last element of the previous vector or any but the last of said initial values exceed a limit formed as the sum of the gap open penalty and gap extension penalty parameters, and
    (iii) computing the vector element values without taking potential gaps in the direction of the vector into account if no dependency is detected, and
    (iv) recursively computing the optimized values by taking potential gaps in the direction of the vector into account if dependency is detected, and
  f) use a maximum range of values in the storage element representing one of said K elements, comprising applying only non-negative values in the processing of said K elements, by adding a bias if the starting value is negative, applying only unsigned arithmetic in the processing of said K elements, and subtracting the same bias later on, said bias being equal to the absolute value of the largest representation of negative value in the element storing said one of said K elements, and
  (g) circuitry for displaying said score S to a user interface, and wherein the circuitry performing the dependency determination further comprises:

circuitry operable to calculate initial score values for the K elements of the said one vector by ignoring any effect that could have resulted from potential gaps in the sequence in the direction of the said vector; and then determine if dependency is possible by checking whether a last element of a previous vector or any but the last of said initial values exceed a limit formed as the sum of the gap open penalty and gap extension penalty parameters, and wherein a circuitry determining final score values of the K elements of the said one vector further comprises:

a microprocessor using as the said final score values the said initial score values computed if no dependency is detected; and a microprocessor recursively recomputing the dependent vector elements taking possible gaps into account if dependency is detected.

10. An electronic device of type ASIC (Application Specific Integrated Circuitry) providing measuring of similarity between two polynucleotide sequences or two amino acid sequences, the two sequences represented as a sequence A of M elements and a sequence B of N elements wherein means in the ASIC provide a Smith-Waterman optimal local alignment similarity score implemented algorithm calculating a S score based on alignment of a matrix H of M times N elements by using a substitution score value matrix Z, and an open penalty gap q and a gap extension penalty r, wherein means in the ASIC for the calculation of alignment matrix H comprises means that:

a) allocate K elements located sequentially on the same row or column in the alignment matrix H, and b) create vectors V with the K elements where the vectors V are represented as registers or processing elements in a microprocessor, that can execute the computer instructions, and c) include means for parallel processing of the K elements, and d) report at least score S; and e) the electronic device further comprises circuitry for determining if the calculation of the value of any one of the said K elements in one of said vectors is dependent on the value of any of the different K−1 elements in said one vector or on a value in an element from a different vector, including circuitry for:

(i) calculating initial score values for the K elements of the said vector by ignoring any effect that could have resulted from potential gaps in the sequence in the direction of the said vector; and (ii) determining if dependency is possible by checking whether the last element of the previous vector or any but the last of said initial values exceed a limit formed as the sum of the gap open penalty and gap extension penalty parameters, and (iii) computing the vector element values without taking potential gaps in the direction of the vector into account if no dependency is detected, and (iv) recursively computing the optimized values by taking potential gaps in the direction of the vector into account if dependency is detected, and f) use a maximum range of values in the storage element representing one of said K elements, comprising applying only non-negative values in the processing of said K elements, by adding a bias if the starting value is negative, applying only unsigned arithmetic in the processing of said K elements, and subtracting the same bias later on, said bias being equal to the absolute value of the largest representation of negative value in the element storing said one of said K elements, and (g) circuitry for displaying said score S to a user interface, and the electronic device further comprising: a microprocessor handling overflow in one storage element including said one K element by employing saturated arithmetic to detect overflow in score calculations, and, if overflow is detected, the entire alignment score is subsequently recomputed using a wider score range in the storage element including the said one K element that is wider than the score range used in the storage element including the said one K element when overflow is detected.

11. The electronic device of claim 10 further comprising:

a microprocessor detecting overflow in said arithmetic operations by applying saturated arithmetic and adjusting the value to the maximum representation of value in the storage element representing said one of said K elements when overflow of the data type of the storage element occurs, thereby detecting overflow by recognizing this said maximum representation of value in said storage element.

* * * * *